US00PP27217P2

(12) United States Plant Patent
Probst

(10) Patent No.: US PP27,217 P2
(45) Date of Patent: Sep. 27, 2016

(54) ***COREOPSIS* PLANT NAMED 'RADIOACTIVE'**

(50) Latin Name: ***Coreopsis* hybrid**
Varietal Denomination: Radioactive

(71) Applicant: Darrell R. Probst, Hubbardston, MA (US)

(72) Inventor: Darrell R. Probst, Hubbardston, MA (US)

( * ) Notice: Subject to any disclaimer, the term of this patent is extended or adjusted under 35 U.S.C. 154(b) by 265 days.

(21) Appl. No.: 14/121,029

(22) Filed: Jul. 22, 2014

(51) Int. Cl.
*A01H 5/02* (2006.01)

(52) U.S. Cl.
USPC ..... Plt./417

(58) Field of Classification Search
USPC ..... Plt./417
See application file for complete search history.

*Primary Examiner* — June Hwu
(74) *Attorney, Agent, or Firm* — Penny J. Aguirre

(57) ABSTRACT

A new cultivar of hybrid *Coreopsis* named 'Radioactive' that is characterized by its large inflorescences with ray florets having an upper surface with a base color that is gold and heavily suffused with scarlet red with an overall effect of red-orange with golden tips appearing when plants are grown under hot temperatures and having a lower surface that has red centers and gold margins, its vigorous growth habit with healthy foliage, its low growing plant habit, spreading outward from above ground stems that are well branched without the need for pinching, its very good resistance to powdery mildew and leaf spot, and its reliably perennial habit in U.S.D.A. Zone 5.

2 Drawing Sheets

Botanical classification: *Coreopsis* hybrid.
Variety denomination: 'Radioactive'.

BACKGROUND OF THE INVENTION

The present invention relates to a new and distinct cultivar of *Coreopsis* plant, botanically of hybrid origin and known as *Coreopsis* 'Radioactive' and will be referred to hereinafter by its cultivar name, 'Radioactive'. The new cultivar of *Coreopsis* is an herbaceous perennial grown for landscape and container use.

The new cultivar was discovered by the Inventor in July of 2013 as a naturally occurring branch mutation of *Coreopsis* 'Mercury Rising' (U.S. Plant Pat. No. 24,689) that was growing in a container in Kensington, Conn. The mutation occurred on one half of the plant in the one-gallon container when it was discovered.

Asexual propagation of the new cultivar was first accomplished by stem cuttings under the direction of the Inventor in Kensington, Conn. in July of 2013. Asexual propagation by stem cuttings and division has determined that the characterisitcs of the new cultivar are stable and are reproduced true to type in successive generations.

SUMMARY OF THE INVENTION

The following traits have been repeatedly observed and are determined to be the characteristics of the new cultivar. These attributes in combination distinguish 'Radioactive' as a unique cultivar of *Coreopsis*.

1. 'Radioactive' exhibits large inflorescences with ray florets having an upper surface with a base color that is gold and heavily suffused with scarlet red for an overall red-orange effect with golden tips appearing when plants are grown under hot temperatures and having a lower surface that has red centers and gold margins.

2. 'Radioactive' exhibits a vigorous growth habit with healthy foliage.
3. 'Radioactive' exhibits a low growing plant habit, spreading outward from above ground stems that are well branched without the need for pinching.
4. 'Radioactive' exhibits very good resistance to powdery mildew and leaf spot.
5. 'Radioactive' is reliably perennial in U.S.D.A. Zone 5.

'Radioactive' has been observed to be botanically similar to 'Mercury Rising' with the exception of ray florets coloration. 'Mercury Rising' differs from 'Radioactive' in having ray florets with a base color that is white and suffused with red with an overall effect of burgundy red with white tips appearing when growing under hot temperatures on the upper surface and red centers with white margins on the lower surface. 'Radioactive' can be compared to *Coreopsis* cultivars 'Redshift' (U.S. Plant Pat. No. 20,412) and 'Center Stage' (U.S. Plant Pat. No. 22,707). 'Redshift' differs from 'Radioactive' in having inflorescences that are light yellow in color with a red eye for most of the season (turns more red in cool temperatures in fall) and in having a more upright plant habit. 'Center Stage' differs from 'Radioactive' in having ray florets that are longer, narrower, less overlapping and crimson red in color with some white coloration to the tips.

BRIEF DESCRIPTION OF THE DRAWINGS

The accompanying color photograph illustrates the overall appearance and distinct characteristics of the new *Coreopsis*. The photographs were taken of six month-old plants as grown in one-gallon containers in Kensington, Conn.

The photograph in FIG. 1 provides a view of 'Radioactive' in bloom.

Figure 1:
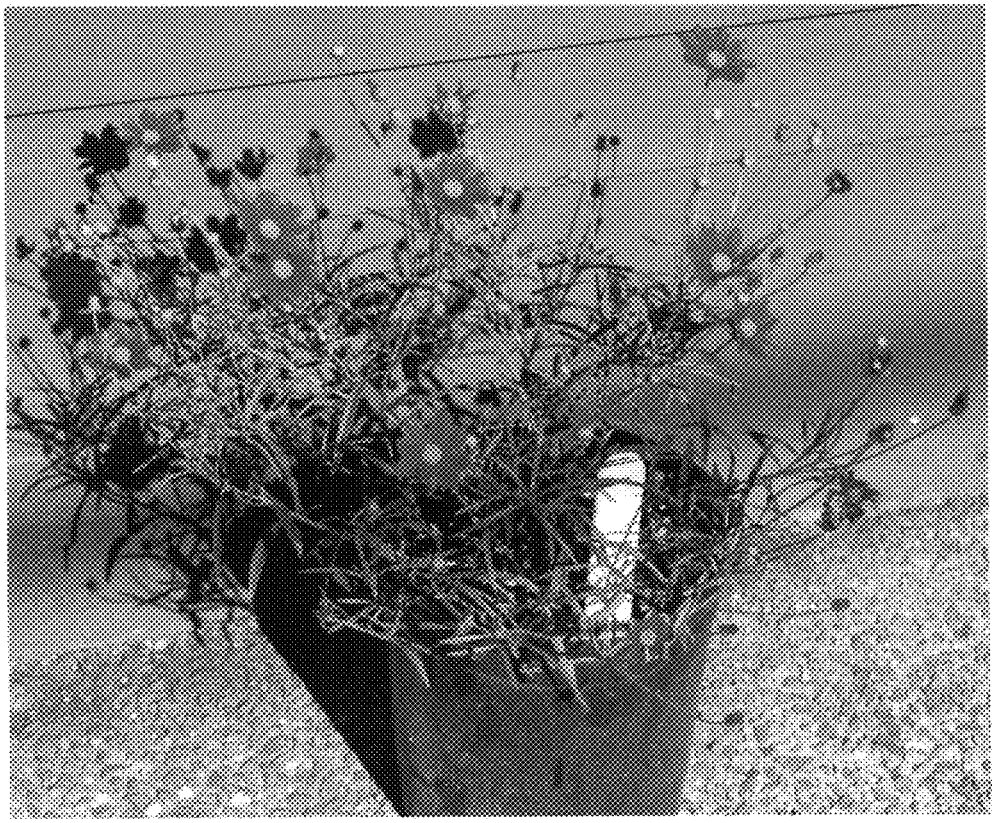
Figure 2:
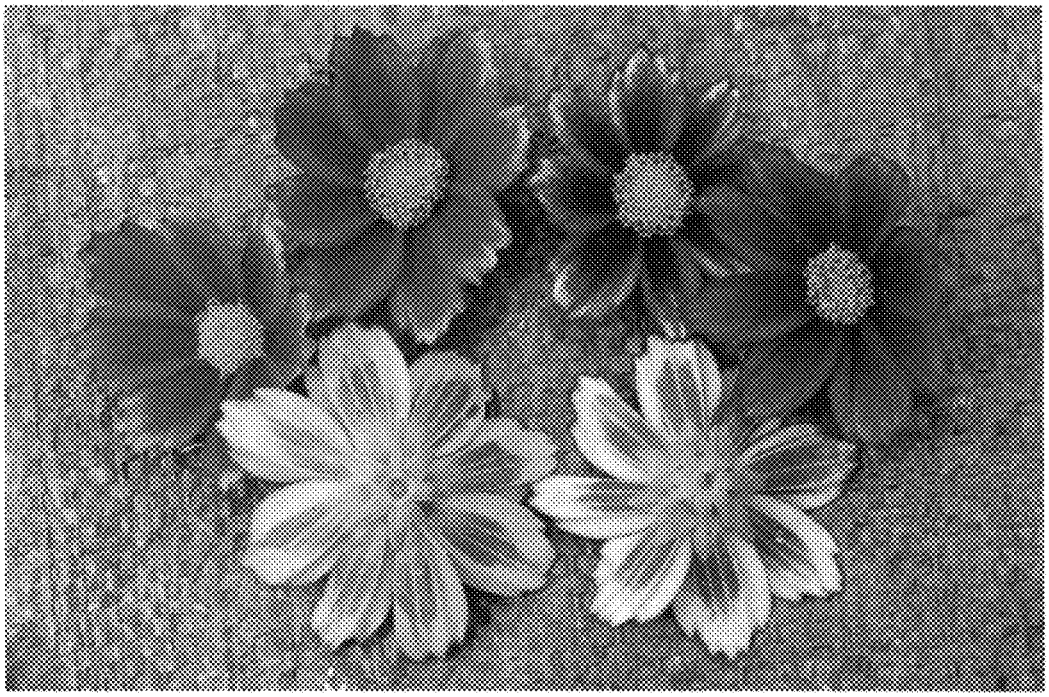

The photograph in FIG. 2 provides a comparison of the inflorescences of 'Radioactive' and 'Mercury Rising'; two inflorescences of 'Radioactive' showing the upper surface on the upper left, one inflorescence of 'Radioactive' showing the lower surface on the lower left, two inflorescence of 'Mercury Rising' showing the upper surface on the upper right, and one inflorescence of 'Mercury Rising' showing the lower surface on the lower right.

The colors in the photograph may differ slightly from the color values cited in the detailed botanical description, which accurately describe the colors of the new *Coreopsis*.

DETAILED BOTANICAL DESCRIPTION

The following is a detailed description of six month-old plants of the new cultivar as grown in one-gallon containers in Kensington, Conn. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—Blooms from June until hard frost in central Massachusetts.

*Plant habit.*—Herbaceous perennial, clump forming, densely branched above ground stems that spread outward.

*Height and spread.*—Reaches about 45 cm in height in bloom and 90 cm in width in the landscape after one year.

*Cold hardiness.*—At least in U.S.D.A. U.S.D.A. Zone 5.

*Diseases resistance.*—Has been observed to be highly resistant to powdery mildew and leaf spot.

*Root description.*—Fibrous when young.

*Propagation.*—Terminal stem cuttings.

*Growth rate.*—Vigorous.

Stem description:

*Shape.*—Oval, ridged.

*Stem color.*—Between 144A and 137C.

*Stem size*—Main stems; an average of 30 cm in length (excluding terminal peduncle) and 3 mm in width, secondary; average of 13 cm in length and 2.5 mm in width.

*Stem surface.*—Glabrous.

*Stem aspect.*—Outward.

*Branching habit.*—Well-branched, an average of 20 main branches, 4 secondary branches per main stem.

*Internode length.*—An average of 5.5 cm.

Foliage description:

*Leaf division.*—Simple.

*Leaf margins.*—Entire to trifid.

*Leaf size.*—Variable, up to 8.3 cm in length and 8 mm in width when entire, up to 9 cm in length and 5.2 cm in width when tri-fid.

*Leaf shape.*—Lanceolate when entire, lanceolate lobes when tri-fid.

*Leaf base.*—Truncate to stem.

*Leaf apex.*—Acute.

*Leaf venation.*—Pinnate, not prominent, matches leaf color on upper and lower surface.

*Leaf attachment.*—Sessile.

*Leaf arrangement.*—Opposite.

*Leaf surface.*—Glabrous on upper and lower surface.

*Leaf color.*—Young and mature upper surface; color between 137A and N137C, young and mature lower surface; color between 137B and 137C.

Inflorescence description:

*Inflorescence type.*—Composite with a single row of ray florets surrounding disk florets in the center, forming a radiant head, inflorescences are borne on branch terminals in loose corymbs.

*Lastingness of inflorescence.*—8 to 10 days until senescence of ray florets, longer in cool temperatures, bracts and disk florets are persistent.

*Fragrance.*—None detected.

*Quantity of inflorescences.*—An average of 48 per main branch.

*Inflorescence size.*—Corymbs; an average of 15 cm in width and height, composite; an average of 1.4 cm in depth and up to 4.8 cm in diameter with disk portion an average of 1 cm in diameter.

*Inflorescence buds.*—Average of 1.3 cm in depth and in diameter, spherical in shape, color; 11B at apex and blending into 144A at base, outer bracts a blend of 144A and 138A.

*Peduncle.*—Corymb; an average of 6 cm in length and 2.5 mm in width, glabrous surface, between 144A and 137C in color, composite; an average of 10 cm in length and 1.4 cm in width, between 144A and 137C in color, surface glabrous.

Involucral bracts:

*Bract number.*—Two rows of 8.

*Bract arrangement.*—Outer bracts are un-fused and held slightly upward, inner bracts surround receptacle with a campanulate form with apical portion un-fused, spreading, and held close to lower surface of ray florets.

*Bract size.*—Outer bracts; an average of 5 mm in length and 1.5 mm in width, inner bracts; up to 8 cm in length and 4 mm in width with free portion an average of 6 mm in length and 4 mm in width.

*Bract color.*—Inner bracts N144A with 144A blended at the base and outer bracts a blend of 144A and 138A.

*Bract texture.*—Glabrous on outer and inner surfaces of outer and inner bracts.

*Bract apex.*—Acute on outer and inner bracts.

*Bract base.*—Truncate on inner and outer bracts.

*Bract margins.*—Entire.

*Bract shape.*—Outer bracts; lanceolate, inner bracts; narrowly elliptic.

Ray florets (sterile):

*Number.*—An average of 8 arranged primarily in one row.

*Shape.*—Oblong.

*Size.*—An average of 1.8 cm in length and 9 mm in width.

*Apex.*—2 to 3 notched.

*Base.*—Broadly cuneate.

*Margins.*—Entire with apex notched.

*Aspect.*—Held horizontal to slightly upward.

*Texture.*—Glabrous on inner and outer surfaces.

*Color.*—Opening and mature upper surface; 14B and heavily suffused with 46A and 46B for an overall effect of 42A, apex is 14A in color when plants are grown under hot temperatures with the amount of apex coloration increasing in extreme heat, opening and mature lower surface; 14B with thick bands of 42A with veins 14B.

Disk florets (perfect):

*Shape.*—Tubular, corolla is fused, flared at apex.

*Number.*—About 200.

*Size.*—About 9 mm in length and 1 mm in width.

*Color.*—En masse; 23A, corolla; base of tube is 18B in color, flared portion is 23A and translucent.

*Receptacle.*—About 5 mm in diameter and 2 mm in depth, 145C in color.

Reproductive organs:

*Presence.*—Disk florets are perfect, ray florets are sterile.

*Gynoecium.*—1 Pistil, 7 mm in length, style is very fine and about 18A in color and translucent, bifid pilose stigma is 19A in color with branches about 0.6 mm in length and recurved, ovary is 1.5 mm in length, 0.5 mm in width, inferior, and 145B in color.

*Androcoecium.*—5 stamens, fused into tube surrounding style, 2 mm in length and 0.5 mm in width, about 164B in color, pollen is low in quantity and 24A in color.

*Fruit/seed.*—No fruit or seed development was observed.

It is claimed:

1. A new and distinct cultivar of *Coreopsis* plant named 'Radioactive' as herein illustrated and described.

* * * * *